United States Patent
Grollier et al.

[11] Patent Number: 5,180,396
[45] Date of Patent: * Jan. 19, 1993

[54] PROCESS FOR DYEING KERATINOUS FIBRES WITH OXIDATION DYES COMBINED WITH INDOLE DERIVATIVES AND DYEING COMPOSITION EMPLOYED

[75] Inventors: Jean F. Grollier, Paris; Jean Cotteret, Verneuil sur Seine; Didier Garoche, Levallois Perret, all of France

[73] Assignee: L'Oreal, Paris, France

[*] Notice: The portion of the term of this patent subsequent to Jan. 22, 2008 has been disclaimed.

[21] Appl. No.: 795,344

[22] Filed: Nov. 20, 1991

Related U.S. Application Data

[63] Continuation of Ser. No. 284,739, Dec. 15, 1988, abandoned.

[30] Foreign Application Priority Data

Dec. 18, 1987 [LU] Luxembourg ............................ 87086

[51] Int. Cl.$^5$ ................................................. A61K 7/13
[52] U.S. Cl. ........................................... 8/405; 8/406; 8/423; 8/424; 8/634; 424/70
[58] Field of Search .................... 8/405, 406, 423, 424, 8/634; 424/70

[56] References Cited

U.S. PATENT DOCUMENTS

| | | | |
|---|---|---|---|
| 1,677,508 | 7/1925 | Winogradoff | 8/405 |
| 4,361,421 | 11/1982 | Bugaut et al. | 8/407 |
| 4,619,160 | 3/1972 | Kalafissis et al. | 8/409 |
| 4,620,850 | 11/1986 | Bachmann et al. | 8/406 |
| 4,716,857 | 10/1988 | Carroll et al. | 8/423 |
| 4,804,385 | 2/1989 | Grollier et al. | 8/423 |
| 4,808,190 | 2/1989 | Grollier et al. | 8/423 |
| 4,822,375 | 4/1989 | Lang et al. | 8/423 |

FOREIGN PATENT DOCUMENTS 2028818 12/1970 Fed. Rep. of Germany .
3031709 4/1982 Fed. Rep. of Germany .

OTHER PUBLICATIONS

Zviak, *The Science of Hair Care*, Dekker, Inc. 1986, pp. 263-267.

*Primary Examiner*—A. Lionel Clingman
*Assistant Examiner*—William S. Parks
*Attorney, Agent, or Firm*—Cushman, Darby & Cushman

[57] ABSTRACT

Process for dyeing keratinous fibres, characterized in that at least one composition (A) containing, in a medium suitable for dyeing, at least one indole derivative and at least one oxidation dye chosen from rapid oxidation dyes and couplers in combination, either (a) with iodide ions, or (b) with hydrogen peroxide, is applied on these fibres at a pH of between 2 and 7, and preferably between 2 and 5, the application of the composition (A) being preceded or followed by the application of a composition (B) which contains, in a medium suitable for dyeing:
either (a) hydrogen peroxide at a pH of between 2 and 12 and preferably between 2 and 7 when (A) contains iodide ions;
or (b) iodide ions at a pH of between 3 and 11 when the composition (A) contains hydrogen peroxide.

34 Claims, No Drawings

PROCESS FOR DYEING KERATINOUS FIBRES WITH OXIDATION DYES COMBINED WITH INDOLE DERIVATIVES AND DYEING COMPOSITION EMPLOYED

This is a continuation of Application Ser. No. 07/284,739, filed Dec. 15, 1988 now abandoned.

The invention relates to a new process for dyeing keratinous fibers, especially human keratinous fibers such as the hair, with indole derivatives combined with certain oxidation dyes chosen from so-called "rapid" oxidation dyes and couplers, and to the compositions employed in this process.

There has been described, in U.S. patent applications Ser. Nos. 198,806 and 198,807 filed on May 25, 1988 a process for dyeing keratinous fibers essentially characterized in that at least one composition (A) containing, in a medium suitable for dyeing, at least one oxidation dye in combination with iodide ions is applied on these fibers, the application of the composition (A) being preceded or followed by the application of a composition (B) which contains, in a medium suitable for dyeing, hydrogen peroxide at a pH of between 2 and 12.

Many processes are, moreover, known for dyeing keratinous fibers, especially the hair, employing 5,6-dihydroxyindole, and more especially a process that consists in dyeing hair in two distinct stages, applying on the hair a composition containing 5,6-dihydroxyindole in combination with iodide ions in a medium suitable for dyeing, this application being preceded or followed by the application of hydrogen peroxide. Such a process is described, in particular, in French Patent Application No. 2,593,061.

The Applicants discovered that they could obtain especially noteworthy colorations in a sufficiently broad palette of varied tints having glints, in particular varied hues of chestnut brown and of blond, these colorations being especially sought after in hair dyeing, by using certain oxidation dyes described in earlier Patent Application Ser. No. 198,806 and Ser. No. 198,807 in combination with 5,6 -dihydroxyindole or its derivatives.

They found, moreover, that the varied hues thereby obtained showed improved resistance to external agents including, in particular, greater resistance to light and/or to washing compared with the colorations obtained using the compositions described previously containing either the oxidation dye or the indole derivative. This result is especially noteworthy when the indole derivative is used in compositions containing oxidation dyes which, in themselves, give, on development, relatively light colorations not possessing much depth, whereas depth is generally desired in hair dyeing.

The subject of the invention is hence the use of 5,6-dihydroxyindole or one of its derivatives in combination with at least one oxidation dye selected from the group consisting of so-called "rapid" oxidation dyes and couplers.

Another subject of the invention consists of the compositions employed during this process.

The subject of the invention is also multi-compartment devices or "kits" comprising the different compositions suitable for carrying out the process according to the invention.

Other subjects of the invention will become apparent on reading the description and the examples which follow.

The process for dyeing keratinous fibers, preferably human keratinous fibers, according to the invention, is essentially characterized in that at least one composition (A) containing, in a medium suitable for dyeing, at least one indole derivative and at least one oxidation dye selected from the group consisting of so-called "rapid" oxidation dyes and couplers is applied on these fibers in combination, either (a) with iodide ions, or (b) with hydrogen peroxide, the application of this composition (A) being preceded or followed by the application of a composition (B) which contains, in a medium suitable for dyeing, either (a) hydrogen peroxide at a pH of between 2 and 12 and preferably between 2 and 7 when the composition (A) contains iodide ions;

or (b) iodide ions at a pH of between 3 and 11 when the composition (A) contains hydrogen peroxide.

The pH of the composition (A), when it contains hydrogen peroxide, is preferably between 2 and 7, and especially between 2 and 5.

The application of the compositions (A) and (B) is optionally separated by a rinse.

The preferred process consists in applying on the fibers a composition (A) containing both an indole derivative and the oxidation dye in combination with iodide ions, the application of this composition (A) being preceded or followed by the application of a composition (B) containing hydrogen peroxide.

In the process according to the invention, the indole derivative corresponds to the formula:

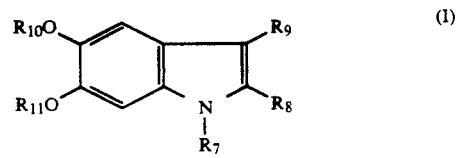

in which:

$R_7$ denotes a hydrogen atom, a lower alkyl group or a group $-SiR_{12}R_{13}R_{14}$;

$R_8$ and $R_9$, which may be identical or different, denote a hydrogen atom or alternatively a lower alkyl group, a carboxyl group, a lower alkoxycarbonyl group or a group $-COOSiR_{12}R_{13}R_{14}$;

$R_{10}$ and $R_{11}$, which may be identical or different, denote a hydrogen atom, a $C_1-C_{20}$ linear or branched alkyl group, a formyl group, a linear or branched $C_2-C_{20}$ acyl group, linear or branched $C_3-C_{20}$ alkenoyl group, a group $-SiR_{12}R_{13}R_{14}$, a group $-P(O)(OR_{15})_2$ or a group $R_{15}OSO_2$, or alternatively $R_{10}$ and $R_{11}$, together with the oxygen atoms to which they are attached, form a ring optionally containing a carbonyl group, a methylene group, a thiocarbonyl group or a group:

$>P(O)OR_{15}$ or alternatively $>CR_{16}R_{17}$;

$R_{15}$ and $R_{16}$ denote a hydrogen atom or a lower alkyl group, $R_{17}$ denoting a lower alkoxy group or a mono- or dialkylamino group, $R_{12}$, $R_{13}$ and $R_{14}$, which may be identical or different, denoting linear or branched lower alkyl groups, and the addition salts with inorganic or organic acids as well as the corresponding salts of alkali metals, alkaline-earth metals or amines.

The lower alkyl or alkoxy radicals preferably denote $C_1-C_6$ radicals.

Among the preferred compounds of the invention, 5,6-dihydroxyindole, 2-methyl-5,6-dihydroxyindole, 5-methoxy-6-hydroxyindole, (5 or 6)-acetoxy-(6 or 5)-hydroxyindole or 2-carboxy-5,6-dihydroxyindole 3-methyl 5,6-dihydroxyindole, 2,3-dimethyl 5,6-dihydroxyindole will be mentioned The iodide ion is preferably an alkali metal, alkaline-earth metal or ammonium iodide, and especially potassium iodide.

So-called "rapid" oxidation dyes are molecules having a benzene structure, dye precursors, capable of generating colored compounds by simple oxidation in the air during the exposure time on the hair, that is to say generally less than 1 hour, this occurring in the absence of another oxidizing agent. They are chosen, in particular, from trihydroxylated derivatives of benzene, diaminohydroxybenzenes, aminodihydroxybenzenes, triaminobenzenes, aminohydroxybenzenes and substituted 1,2-dihydroxybenzenes.

Among trihydroxylated derivatives of benzene, there may be mentioned 1,2,4-trihydroxybenzene, 1,2,4-trihydroxy-5-alkylbenzenes in which the alkyl group is a $C_1$-$C_8$ lower alkyl group and 1,2,3-trihydroxybenzene and their salts.

Among diaminohydroxybenzenes, there may be mentioned 2,4-diaminophenol, 2,5-diamino-4-methoxy-1-hydroxybenzene and their salts.

Among aminodihydroxybenzenes, there may be mentioned 2-amino-1,4-dihydroxybenzene, 1,4-dihydroxy-2-diethylaminobenzene, 4-aminoresorcinol and their salts.

Among substituted 1,2-dihydroxybenzenes, lower C1-C6 alkyl or lower C1-C6 alkoxy substituted 1,2-dihydroxybenzene are preferred.

The aminohydroxybenzenes are chosen, in particular, from 2-amino-4-methoxyphenol, 2-aminophenol, 4,6-dimethoxy-3-amino-1-hydroxybenzene, 2,6-dimethyl-4-[N-(p-hydroxyphenyl)amino]-1-hydroxybenzene and their salts.

As representative triaminobenzenes, there may be mentioned 1,5-diamino-2-methyl-4-[N-(p-hydroxyphenyl)amino]benzene and its salts.

The modifiers or couplers are compounds that are known to react with oxidation bases, also known as oxidation dye precursors, by an oxidative condensation process, giving colored compounds specific to the base and the coupler in question. This reaction is referred to as "coupling". They are chosen from phenols, meta-diphenols, meta-aminophenols, ortho-diphenol, meta-phenylenediamines, mono- or polyhydroxylated derivatives of naphthalene and of aminonaphthalene, pyrazolones and benzomorpholines.

Among the couplers or modifiers, there may, in particular, be mentioned compounds corresponding to the formula (II)

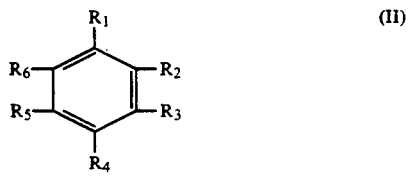

in which:
  $R_1$ denotes hydroxy or an amino group that can be substituted with one or more $C_1$-$C_6$ hydroxyalkyl groups; $R_3$ and $R_5$, independently of one another, can denote hydrogen, OH, an amino group optionally substituted with a $C_1$-$C_6$ lower hydroxyalkyl group or a $C_1$-$C_6$ lower alkyl group; $R_2$, $R_4$ and $R_6$ can denote a hydrogen atom or a $C_1$-$C_6$ alkoxy group, a hydroxyalkoxy group or a $C_1$-$C_6$ lower alkyl group; it also being possible for $R_3$ and $R_4$ together to form a methylenedioxy group.

Among especially preferred couplers, there may be mentioned 3-amino-6-methylphenol, 3-aminophenol, 1,3-dihydroxybenzene, 1,2-dihydroxybenzene, 2-methoxy-5-aminophenol, 2-methoxy-5-[N-(2-hydroxyethyl)amino]phenol, 1,3-diamino-2,6-dimethoxybenzene, 2-methoxy-1-(N-methylamino)-4-(2-hydroxyethyloxy)aminobenzene, 1,3-diamino-6-methoxybenzene, 1,3-diamino-4,6-dimethoxybenzene, 4,6-dimethoxy-1,3-bis[N-(2-hydroxyethyl)amino]benzene, 2,6-dimethoxy-3-[N-(2-hydroxyethyl)amino]-1-aminobenzene, 2,4-dimethoxy-3-[N-(2-hydroxyethyl)amino]-1-aminobenzene, 2-methyl-5-[N-(2-hydroxyethyl)amino]phenol, 1,3-bis[N-(2-hydroxyethyl)amino]-4-methoxybenzene, 3-amino-4-methoxyphenol, 3,4-methylenedioxy-1-aminobenzene, 3,4-methylenedioxy-6-methoxy-1-aminobenzene, 2,6-dimethyl-3-[N-(2-hydroxyethyl)amino]phenol, 2,6-dimethyl-3-aminophenol, 4-ethoxy-1-amino-3-[N,N-bis(2-hydroxyethyl)amino]benzene, (2,4-diaminophenoxy)ethanol, [2-amino-4-(N-methylamino)phenoxy]ethanol, 1-methoxy-2-[N-(2-hydroxyethyl)amino]-4-aminobenzene and their salts.

Other preferred couplers are 6-aminobenzomorpholine, 6-hydroxybenzomorpholine, 1-naphthol and 1-amino-7-naphthol and their salts.

These different oxidation dyes are used as mixtures or alone, in combination with iodide ions and indole derivatives.

An especially preferred embodiment of the invention consists in using, in combination with 5,6-dihydroxyindole and iodide ions, at least one trihydroxylated derivative of benzene, such as 1,2,4-trihydroxybenzene or 1,2,4-trihydroxy-5-methylbenzene, or alternatively couplers such as 1,3-dihydroxybenzene, 3-aminophenol, 3-amino-6-methylphenol, 3,4-methylenedioxy-6-methoxy-1-aminobenzene, 1-naphthol or mixtures thereof.

The result obtained with the combination according to the invention is especially surprising in view of the dyeing properties of these oxidation dyes in traditional systems, especially couplers which give rise to a coloration only in the presence of a base or oxidation dye precursor, by an oxidative condensation process.

The subject of the invention is also dyeing compositions intended for use in a process for dyeing keratinous fiber, especially human hair, comprising at least 5,6-dihydroxyindole or one of its derivatives of formula (I), an oxidation dye selected from the group consisting of "rapid" oxidation dyes and couplers, and iodide ions, in a medium suitable for dyeing. The oxidation dyes used in the compositions according to the invention are preferably chosen from the preferred dyes defined above.

The composition (A), containing 5,6-dihydroxyindole or one of its derivatives of formula (I), the oxidation dye and the iodide ions, generally contains the oxidation dye in proportions of between 0.01 and 10% by weight relative to the total weight of composition (A), and preferably between 0.25 and 5% by weight. The 5,6-dihydroxyindole or one of its derivatives of formula (I) is generally present in proportions of between 0.01 and 5% by weight, and preferably between 0.03 and 3% by weight, relative to the total weight of the composition (A). The proportion of iodide in these same compositions is preferably between 0.007 and 4% by weight, expressed as $I^-$ ions, and preferably between 0.08 and 1.5% by weight, expressed as $I^-$ ions, relative to the total weight of the composition (A).

The hydrogen peroxide content used in the compositions (B) is generally between 1 and 40 volumes, and preferably between 2 and 20 volumes, and more especially between 3 and 10 volumes.

The ratio between the indole derivatives of formula (I) in combination with the oxidation dye(s), on the one hand, and the iodide ions, on the other hand, is preferably between 0.05 and 10, and more especially between 0.5 and 2.

The process according to the invention is carried out by arranging exposure times, for the different compositions applied in each of the different steps of the process, of between 10 seconds and 45 minutes, and preferably of the order of 2 to 25 minutes, and more especially of the order of 2 to 10 minutes.

The applicants found, in effect, that the process according to the invention enabled various colorations to be obtained over a wide range of hues capable of being well endowed with glints, the colorations being both rapid and strong, penetrating well into the fiber, and in particular human keratinous fiber such as the hair, without degrading them. These colorations also show an improved resistance to external agents including, more especially, an improved resistance to light and/or to washing compared with processes exclusively employing 5,6-dihydroxyindole or one of its derivatives of formula (I) in combination with iodide ions, or exclusively the oxidation dye in combination with iodide ions.

The applicants were also able to note that hair dyed several times, following regrowth, by means of the processes and the compositions employed according to the invention was softer, more shiny and had good mechanical properties, compared with hair dyed employing the processes and the compositions of the prior art.

By means of the process and the compositions according to the invention, relatively intense colorations are obtained in relatively short times, of the order of 5 to 15 minutes.

The compositions used for carrying out the process according to the invention may be presented in various forms, such as more or less thickened or gelled liquids, creams, emulsions, foams or other forms suitable for carrying out dyeing.

The dyeing compositions designed for use in the process according to the invention, and containing 5,6-dihydroxyindole or one of its derivatives of formula (I) and the oxidation dye in combination with iodide ions generally contain an aqueous medium consisting of water or a water/solvent(s) mixture, the solvent(s) preferably being chosen from organic solvents such as ethyl alcohol, propyl or isopropyl alcohol, tert-butyl alcohol, ethylene glycol, ethylene glycol monomethyl, monoethyl and monobutyl ethers, ethylene glycol monoethyl ether acetate, propylene glycol, propylene glycol and dipropylene glycol monomethyl ethers and methyl lactata. The especially preferred solvents are ethyl alcohol and propylene glycol.

The indole derivatives and the oxidation dyes may also be stored with the iodides in a medium consisting of anhydrous solvents, this composition being mixed at the time of use with an aqueous medium.

When the medium is aqueous, the composition (A) has a pH of between 2 and 7, and preferably between 3.5 and 7.

According to the invention, a solvent comprising less than 1% of water is referred to as an anhydrous solvent.

When the medium consists of a water/solvent(s) mixture, the solvents are present in concentrations preferably of between 0.5 and 75% by weight relative to the total weight of the composition, and especially between 2 and 50%, and more especially between 2 and 20%.

The compositions according to the invention can contain other adjuvants customarily used in the dyeing of keratinous fibers.

In the preferred application to hair dyeing, these compositions can contain, in particular, fatty amides in proportions of 0.05 to 10%, anionic, cationic, nonionic or amphoteric surfactants, or mixtures thereof, present in proportions of between 0.1 and 50% by weight, thickeners, perfumes, sequestering agents, film-forming agents, treatment agents, dispersants, conditioners, preservatives, opacifiers and agents for swelling keratinous fibers.

The thickeners may be chosen, more especially, from sodium alginate, gum arabic, guar gum, biopolymers such as xanthan gum or scleroglucans, cellulose derivatives such as methylcellulose, hydroxyethylcellulose, hydroxypropylmethylcellulose and carboxymethylcellulose sodium salt, and acrylic acid polymers. It is also possible to use inorganic thickening agents such as bentonite. These thickeners, used alone or as mixtures, are preferably present in proportions of between 0.1 and 5% by weight relative to the total weight of the composition, and advantageously between 0.5 and 3%.

The acidifying agents which are usable in the preferred embodiment of the process, employing the compositions at acid pH, may be chosen from lactic acid, acetic acid, tartaric acid, phosphoric acid, hydrochloric acid and citric acid.

It is also possible to adjust the pH with alkalinizing agents chosen, in particular, from amines such as alkanolamines, alkylamines and alkali metal or ammonium hydroxides or carbonates, in particular when the precursors are used in the form of salts of strong acids.

When the composition is used in the form of a foam, it may be packaged under pressure in an aerosol device in the presence of a propellant and at least one foam generator. The foam generators can be anionic, cationic, nonionic or amphoteric foaming polymers, or surfactants of the type defined above.

For the purpose of carrying out the process according to the invention, the different compositions may be packaged in a multi-compartment device, also referred to as a dyeing "kit" or outfit, containing all the components designed to be applied for a single dyeing on keratinous fibers in successive applications with or without premixing. Such devices are known per se, and can comprise a first compartment containing the composition (A), containing the indole derivative and the oxidation dye as mentioned above, in the presence of iodide ions in a medium suitable for dyeing, and, in a second compartment, a hydrogen peroxide solution.

When the medium containing the indole derivative, the oxidation dye and the iodide ions is an anhydrous medium, mixing is performed, before use, with an aqueous vehicle suitable for dyeing, present, where appropriate, in a third compartment.

The composition containing the indole derivative, the oxidation dye and the iodide ions in an anhydrous medium can optionally be applied directly on the wet keratinous fibers.

When the composition (A) applied on the fibers contains hydrogen peroxide, the dyeing outfit preferably comprises, in a first compartment a composition (A) containing, in a medium suitable for dyeing, the indole derivative and the oxidation dye as defined above, in a second compartment the composition (B) containing iodide ions, and in a third compartment an aqueous hydrogen peroxide composition, the content of the third compartment being designed to be mixed with the content of the first compartment immediately before use.

When the medium suitable for dyeing is aqueous, the composition of the first compartment preferably has a pH of between 2 and 7, and especially between 3.5 and 7. The pH of the composition containing hydrogen peroxide is between 2 and 12, but it is preferably acid and between 2 and 7, and more especially between 2 and 5.

The multi-compartment devices which are usable according to the invention may be equipped with means, known per se, for mixing at the time of use, and be packaged under an inert atmosphere.

The process and the compositions used according to the invention may be employed for dyeing natural or already dyed hair, permanent-waved or otherwise or straightened, or strongly or lightly bleached and optionally permanent-waved hair. It is also possible to use them for dyeing furs or wool.

The examples which follow are designed to illustrate the invention, no limitation of the latter being implied.

EXAMPLE 1

The following compositions are prepared:

| COMPOSITION $A_1$: | |
|---|---|
| 5,6-Dihydroxyindole | 0.30 g |
| 1,2,4-Trihydroxybenzene | 1.00 g |
| Potassium iodide | 1.00 g |
| Ethyl alcohol | 10.00 g |
| Guar gum, sold by the company CELANESE under the name "JAGUAR HP 60" | 1.00 g |
| Glycoside alkyl ether, sold at a concentration of 60% AS by the company SEPPIC under the name "TRITON CG 110" | 5.00 g AS |
| Preservative qs | |
| Natural pH 5.8 | |
| Water | qs 100.00 g |

| COMPOSITION B containing 12.5 volumes of hydrogen peroxide | |
|---|---|
| Hydrogen peroxide | 3.75 g |
| Ammonium lauryl sulphate | 6.70 g |
| Gum arabic | 1.00 g |
| Stabilizer | 0.03 g |
| Perfume qs | |
| 2-Amino-2-methyl-1-propanol qs pH 4 | |
| Water | qs 100.00 g |

The dyeing of 90% white natural hair is performed by applying the composition ($A_1$).

The composition ($A_1$) is left in place for 15 minutes. After rinsing with water, the "12.5 volumes" hydrogen peroxide composition (B) is applied and left to act for 5 minutes. After rinsing with water and shampooing, the hair is dyed a golden light chestnut brown with red glints.

EXAMPLE 2

The following composition is prepared:

| COMPOSITION $A_2$: | |
|---|---|
| 5,6-Dihydroxyindole | 0.60 g |
| 1,3-Dihydroxybenzene | 0.05 g |
| 3-Aminophenol | 0.40 g |
| Potassium iodide | 1.00 g |
| Ethyl alcohol | 10.00 g |
| Guar gum, sold by the company CELANESE under the name "JAGUAR HP 60" | 1.00 g |
| Glycoside alkyl ether, sold at a concentration of 60% AS by the company SEPPIC under the name "TRITON CG 110" | 5.00 g AS |
| Preservative qs | |
| Natural pH 6.5 | |
| Water | qs 100.00 g |

The dyeing of 90% white permanent-waved hair is performed by applying the composition ($A_2$).

The composition is left in place for 15 minutes. After rinsing with water, a "12.5 volumes" hydrogen peroxide composition (B) is applied and left to act for 5 minutes. After rinsing with water and shampooing, the hair is dyed a dark chestnut brown with a natural glint.

EXAMPLE 3

The following composition is prepared:

| COMPOSITION $A_3$: | |
|---|---|
| 5,6-Dihydroxyindole | 0.20 g |
| 3-Aminophenol | 0.10 g |
| Potassium iodide | 1.00 g |
| Ethyl alcohol | 10.00 g |
| Guar gum, sold by the company CELANESE under the name "JAGUAR HP 60" | 1.00 g |
| Glycoside alkyl ether, sold at a concentration of 60% AS by the company SEPPIC under the name "TRITON CG 110" | 5.00 g AS |
| Preservative qs | |
| Natural pH 7 | |
| Water | qs 100.00 g |

The dyeing of 90% white natural hair is performed by applying composition $A_3$.

The composition is left in place for 15 minutes. After rinsing with water, a "12.5 volumes" hydrogen peroxide composition (B) is applied and left to act for 5 minutes. After rinsing with water and shampooing, the hair is dyed a golden blond with a natural glint.

EXAMPLE 4

The following composition is prepared:

| COMPOSITION $A_4$: | |
|---|---|
| 5,6-Dihydroxyindole | 0.70 g |
| 1,2,4-Trihydroxy-5-methylbenzene | 3.00 g |
| Potassium iodide | 2.00 g |
| Ethyl alcohol | 10.00 g |
| Guar gum, sold by the company CELANESE under the name "JAGUAR HP 60" | 1.00 g |
| Glycoside alkyl ether, sold at a concentration of 60% AS by the company SEPPIC under the name "TRITON CG 110" | 5.00 g AS |
| Preservative qs | |

| COMPOSITION A₄: | |
|---|---|
| Natural pH 5.4 | |
| Water | qs 100.00 g |

The dyeing of 90% white permanent-waved hair is performed by applying the composition (A₄).

The composition is left in place for 15 minutes. After rinsing with water, a "12.5 volumes" hydrogen peroxide composition (B) is applied and left to act for 5 minutes. After rinsing with water and shampooing, the hair is dyed an auburn dark blond.

EXAMPLE 5

The following composition is prepared:

| COMPOSITION A₅: | |
|---|---|
| 5,6-Dihyroxyindole | 0.50 g |
| 1,3-Dihydroxybenzene | 0.50 g |
| Potassium iodide | 1.00 g |
| Ethyl alcohol | 10.00 g |
| Guar gum, sold by the company CELANESE under the name "JAGUAR HP 60" | 1.00 g |
| Glycoside alkyl ether, sold at a concentration of 60% AS by the company SEPPIC under the name "TRITON CG 110" | 5.00 g AS |
| Preservative qs | |
| Triethanolamine qs pH 6 | |
| Water | qs 100.00 g |

The dyeing of 90% white permanent-waved hair is performed by applying the composition (A₅).

The composition is left in place for 15 minutes. After rinsing with water, a "12.5 volumes" hydrogen peroxide composition (B) is applied and left to act for 5 minutes. After rinsing with water and shampooing, the hair is dyed an ash-blond chestnut brown.

EXAMPLE 6

The following composition is prepared:

| COMPOSITION A₆: | |
|---|---|
| 5,6-Dihydroxyindole | 0.20 g |
| 3-Aminophenol | 0.10 g |
| 1,2,4-Trihydroxybenzene | 0.40 g |
| Potassium iodide | 0.50 g |
| Ethyl alcohol | 10.00 g |
| Guar gum, sold by the company CELANESE under the name "JAGUAR HP 60" | 1.00 g |
| Glycoside alkyl ether, sold at a concentration of 60% AS by the company SEPPIC under the name "TRITON CG 110" | 5.00 g AS |
| Preservative qs | |
| Natural pH 6.3 | |
| Water | qs 100.00 g |

The dyeing of 90% white natural hair is performed by applying the composition (A₆).

The composition is left in place for 15 minutes. After rinsing with water, a "12.5 volumes" hydrogen peroxide composition (B) is applied and left to act for 5 minutes. After rinsing with water and shampooing, the hair is dyed a slightly ashen golden blond.

EXAMPLE 7

The following composition is prepared:

| COMPOSITION A₇ | |
|---|---|
| 5,6-Dihydroxyindole | 0.30 g |
| 3-Amino-6-methylphenol | 0.30 g |
| 1,2,4-Trihydroxybenzene | 0.30 g |
| Potassium iodide | 0.80 g |
| Ethyl alcohol | 10.00 g |
| Guar gum, sold by the company CELANESE under the name "JAGUAR HP 60" | 1.00 g |
| Glycoside alkyl ether, sold at a concentration of 60% AS by the company SEPPIC under the name "TRITON CG 110" | 5.00 g AS |
| Preservative qs | |
| Natural pH 6.7 | |
| Water | qs 100.00 g |

The dyeing of 90% white natural hair is performed by applying the composition (A₇).

The composition is left in place for 15 minutes. After rinsing with water, a "12.5 volumes" hydrogen peroxide composition (B) is applied and left to act for 5 minutes. After rinsing with water and shampooing, the hair is dyed a russet brown.

EXAMPLE 8

The following composition is prepared:

| COMPOSITION A₈ | |
|---|---|
| 5,6-Dihydroxyindole | 0.40 g |
| 1-Naphthol | 0.40 g |
| Potassium iodide | 0.80 g |
| Ethyl alcohol | 10.00 g |
| Guar gum, sold by the company CELANESE under the name "JAGUAR HP 60" | 1.00 g |
| Glycoside alkyl ether, sold at a concentration of 60% AS by the company SEPPIC under the name "TRITON CG 110" | 5.00 g AS |
| Preservative qs | |
| Triethanolamine qs pH 8.5 | |
| Water | qs 100.00 g |

The dyeing of 90% white natural hair is performed by applying the composition (A₈).

The composition is left in place for 15 minutes. After rinsing with water, a "12.5 volumes" hydrogen peroxide composition (B) is applied and left to act for 5 minutes. After rinsing with water and shampooing, the hair is dyed a light chestnut brown with an ashen glint.

EXAMPLE 9

The following composition is prepared:

| COMPOSITION A₉ | |
|---|---|
| 5,6-Dihyroxyindole | 0.30 g |
| 3,4-Methylenedioxy-6-methoxy-1-aminobenzene | 0.30 g |
| Potassium iodide | 0.50 g |
| Ethyl alcohol | 10.00 g |
| Guar gum, sold by the company CELANESE under the name "JAGUAR HP 60" | 1.00 g |
| Glycoside alkyl ether, sold at a concentration of 60% AS by the company SEPPIC under the name "TRITON CG 110" | 5.00 g AS |
| Preservative qs | |
| Triethanolamine qs pH 6 | |
| Water | qs 100.00 g |

The dyeing of 90% white natural hair is performed by applying the composition (A₉).

The composition is left in place for 15 minutes. After rinsing with water, a "12.5 volumes" hydrogen peroxide composition is applied and left to act for 5 minutes. After rinsing with water and shampooing, the hair is dyed a light chestnut brown.

EXAMPLE 10

The following composition is prepared:

| COMPOSITION $A_{10}$: | |
| --- | --- |
| Sodium iodide | 0.40 g |
| Ethyl alcohol | 5.00 g |
| Propylene glycol | 5.00 g |
| Xanthan gum, sold by the company RHONE POULENC under the name "RHODOPOL SC" | 2.00 g |
| Preservative qs | |
| Triethanolamine qs pH 6.5 | |
| Demineralized water | qs 100.00 g |
| COMPOSITION $B_1$: | |
| 5,6-Dihydroxyindole | 1.00 g |
| 2,4-Diaminophenoxyethanol dihydrochloride | 1.20 g |
| 3-Amino-6-methylphenol | 0.50 g |
| Glycoside alkyl ether sold at a concentration of 60% AS by the company SEPPIC under the name "TRITON CG 110" | 7.50 g AS |
| Xanthan gum, sold by the company RHONE POULENC under the name "RHODOPOL SC" | 3.00 g |
| Ethyl alcohol | 12.00 g |
| Triethanolamine qs pH 6.5 | |
| Demineralized water | qs 100.00 g |

The composition $A_{10}$ is applied for 15 minutes on natural grey hair containing 90% of white hair. A rinsing is performed. A weight-for-weight mixture of the composition $B_1$ with a hydrogen peroxide at pH 3 assaying at 20 volumes, this mixture being prepared at the time of use, is then applied for 15 minutes. The hair is then rinsed and dried. It is colored a slightly ashen natural blond.

EXAMPLE 11

The following composition is prepared:

| COMPOSITION $A_{11}$: | |
| --- | --- |
| 5,6-Dihydroxyindole | 0.45 g |
| 6-Hydroxybenzomorpholine | 0.45 g |
| Ethylene glycol monobutyl ether | 8.50 g |
| Potassium iodide | 0.30 g |
| Hydroxyethylcellulose, sold by the company AQUALON under the name "NATROSOL 250 HHR" | 1.00 g |
| Tartaric acid qs pH 5 | |
| Demineralized water | qs 100.00 g |

Natural grey hair containing 90% of white hair is pretreated for 10 minutes with a hydrogen peroxide composition $B_2$ at pH 3, assaying at 30 volumes. After rinsing, the composition ($A_{11}$) is applied for 20 minutes. After rinsing and drying, the hair is dyed in a very ashen light blond hue. If the intermediate rinse is eliminated, the hue obtained is a pearly ashen dark blond.

EXAMPLE 12

The following composition is prepared:

| COMPOSITION $A_{12}$ | |
| --- | --- |
| 2-Methyl-5,6-dihydroxyindole | 0.70 g |
| hydrobromide | |
| Resorcinol | 0.40 g |
| 3-Aminophenol | 0.10 g |
| 3-Amino-6-methylphenol | 0.25 g |
| Potassium iodide | 0.60 g |
| Ethyl alcohol | 10.00 g |
| Guar gum, sold by the company CELANESE under the name "JAGUAR HP 60" | 1.00 g |
| Glycoside alkyl ether, sold at a concentration of 60% AS by the company SEPPIC under the name "TRITON CG 110" | 5.00 g AS |
| Triethanolamine qs pH 6 | |
| Preservatives qs | |
| Demineralized water | qs 100.00 g |

This composition is applied for 20 minutes on natural grey hair containing 90% of white hair. After rinsing, a hydrogen peroxide composition $B_3$ at pH 3, assaying at 12.5 volumes, is applied for 10 minutes. After rinsing and drying, the hue obtained is an ashen golden light blond.

EXAMPLE 13

Example 12 is repeated, but the pH of the hydrogen peroxide used is brought to 8.5 before use with 2-amino-2-methyl-1-propanol. A very light blond with a golden ashen glint is obtained as the final hue.

EXAMPLE 14

The following composition is prepared:

| COMPOSITION $A_{13}$: | |
| --- | --- |
| 5-Acetoxy-6-hydroxyindole | 0.60 g |
| 6-Aminobenzomorpholine dihydrochloride | 0.80 g |
| 1,2,4-Trihydroxybenzene | 0.40 g |
| Potassium iodide | 1.00 g |
| Ethyl alcohol | 15.00 g |
| Glycoside alkyl ether, sold at a concentration of 60% AS by the company SEPPIC under the name "TRITON CG 110" | 5.00 g AS |
| Xanthan gum, sold by the company RHONE POULENC under the name "RHODOPOL SC" | 1.50 g |
| Preservatives | 0.15 g |
| Triethanolamine qs pH 7 | |
| Demineralized water | qs 100.00 g |

This composition is applied for 12 minutes on natural grey hair containing 90% of white hair, and is then rinsed off. The hair is then treated with a hydrogen peroxide composition $B_3$ at pH 3, assaying at 12.5 volumes, for 8 minutes. After rinsing and drying, the hair is colored in a natural light blond hue with a slightly golden ashen glint.

EXAMPLE 15

Example 14 is repeated, but the pH of the hydrogen peroxide used is brought to 8 before use with triethanolamine. The same final dyeing result is obtained as in Example 14, that is to say a natural light blond hue with a slightly golden ashen glint.

EXAMPLE 16

The following composition is prepared:

| COMPOSITION $A_{14}$: | |
| --- | --- |
| 5,6-Dihydroxyindole | 0.50 g |

COMPOSITION A₁₄ (continued):

| | |
|---|---|
| 1,2,4-Trihydroxybenzene | 0.50 g |
| 3-Aminophenol | 0.15 g |
| Sodium iodide | 0.40 g |
| Ethylene glycol monoethyl ether | 7.50 g |
| Sodium lauryl ether sulphate containing 2 moles of ethylene oxide, sold by the company LEVER in a 30% strength solution in water under the name "SACTIPON 8533" | 3.00 g AS |
| Hydrochloric acid qs pH 5 | |
| Preservatives qs | |
| Demineralized water | qs 100.00 g |

COMPOSITION B₄ containing 12.5 volumes of $H_2O_2$:

| | |
|---|---|
| Hydrogen peroxide | 3.75 g |
| Ammonium lauryl sulphate | 6.70 g |
| Thickener | 1.00 g |
| Stabilizer | 0.03 g |
| Perfume qs | |
| Monoethanolamine qs pH 8.5 | |
| Water | qs 100.00 g |

The composition A₁₄ is applied for 15 minutes on natural grey hair containing 90% of white hair. It is rinsed off and the hydrogen peroxide composition B₄ is applied for 10 minutes. After rinsing and drying, a natural light blond coloration with a slightly ashen glint is obtained.

EXAMPLE 17

The following composition is prepared:

COMPOSITION A₁₅:

| | |
|---|---|
| 5,6-Dihydroxyindole | 0.10 g |
| 4-Methyl-1,2-dihydroxybenzene | 1.00 g |
| Potassium iodide | 1.00 g |
| Ethyl alcohol | 10.00 g |
| Guar gum, sold by the company CELANESE under the name "JAGUAR HP 60" | 1.00 g |
| Glycoside alkyl ether, sold at a concentration of 60% AS by the company SEPPIC under the name "TRITON CG 110" | 5.00 g AS |
| Triethanolamine qs pH 7 | |
| Preservative qs | |
| Water | qs 100.00 g |

The dyeing of 90% white natural grey hair is performed by applying the composition A₁₅, which is left in place for 10 minutes. After rinsing with water, a "10 volumes" hydrogen peroxide composition B₅, pH 3.8, is applied and left to act for 5 minutes. After rinsing with water and shampooing, the hair is dyed blond.

We claim:

1. A process for dyeing keratinous fibers comprising applying to said fibers at least one composition (A) containing in a medium suitable for dyeing said fibers, at least one indole derivative present in an amount ranging from 0.03 to 3 weight percent based on the total weight of said composition (A) and at least one oxidation dye which generates a colored compound by oxidation in air within one hour and a coupler, said oxidation dye being present in an amount ranging from 0.25 to 5 weight percent based on the total weight of said composition (A), in combination with (a) a source of iodide ions present in an amount ranging from 0.08 to 1.5 weight percent, expressed as $I^-$ ions and based on the total weight of said composition (A) or (b) hydrogen peroxide, said composition (A) having a pH ranging from 2 to 7, and the application of said composition (A) is preceded or followed by the application of composition (B) comprising in a medium suitable for dyeing said fibers (a') hydrogen peroxide at a pH ranging from 2 to 12 when said composition (A) contains a source of iodide ions, or (b') a source of iodide ions at a pH ranging from 3 to 11 when said composition (A) contains hydrogen peroxide.

2. The process of claim 1 wherein said composition (A) has a pH ranging from 2 to 5.

3. The process of claim 1 wherein said composition (B) contains hydrogen peroxide at a pH ranging from 2 to 7.

4. The process of claim 1 wherein said composition (A) contains said indole derivative and said oxidation dye in combination with said source of iodide ions and the application of said composition (A) is preceded or followed by the application of said composition (B) containing hydrogen peroxide.

5. The process of claim 1 wherein said indole derivative has the formula

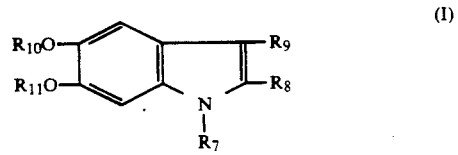

(I)

wherein
$R_7$ represents hydrogen, $C_1$–$C_6$ alkyl or —$SiR_{12}R_{13}R_{14}$;

$R_8$ and $R_9$, each independently, represent hydrogen, $C_1$–$C_6$ alkyl, carboxyl, $C_1$–$C_6$ alkoxy carbonyl or —$COOSiR_{12}R_{13}R_{14}$;

$R_{10}$ and $R_{11}$, each independently, represent hydrogen, linear or branched $C_1$–$C_{20}$ alkyl, formyl, linear or branched $C_2$–$C_{20}$ acyl, linear or branched $C_3$–$C_{20}$ alkenoyl, —$SiR_{12}R_{13}R_{14}$, —$P(O)(OR_{15})_2$ or $R_{15}OSO_2$, or $R_{10}$ and $R_{11}$ together with the oxygen atoms to which they are attached form a ring optionally containing a carbonyl group, a methylene group, a thiocarbonyl group, a>P-(O)$OR_{15}$ group or a>$CR_{16}R_{17}$ group;

$R_{15}$ and $R_{16}$ represent hydrogen or $C_1$–$C_6$ alkyl;

$R_{17}$ represents $C_1$–$C_6$ alkoxy, monoalkylamino or dialkylamino;

$R_{12}$, $R_{13}$ and $R_{14}$, each independently, represent linear or branched $C_1$–$C_6$ alkyl, and the acid addition salt thereof with an inorganic or organic acid or the corresponding alkali metal, alkaline earth metal or amine salt thereof.

6. The process of claim 1 wherein said indole derivative is selected from the group consisting of 5,6-dihydroxyindole, 2-methyl-5,6-dihydroxyindole, 5-methoxy-6-hydroxyindole, 5-acetoxy-6-hydroxyindole, 6-acetoxy-5-hydroxyindole, a mixture of 5-acetoxy-6-hydroxyindole and 6-acetoxy-5-hydroxyindole, 2-carboxy-5,6-dihydroxyindole, 3-methyl-5,6-dihydroxyindole and 2,3-dimethyl-5,6-dihydroxyindole.

7. A process for dyeing keratinous fibers comprising applying to said fibers at least one composition (A) containing in a medium suitable for dyeing said fibers at least 5,6-dihydroxyindole present in an amount ranging from 0.03 to 3 weight percent based on the total weight of said composition (A) and at least one oxidation dye consisting of a rapid oxidation dye which generates a colored compound by oxidation in air within one hour and a coupler, said oxidation dye being present in an amount ranging from 0.25 to 5 weight percent based on the total weight of said composition (A), in combination with a source of iodide ions present in an amount ranging from 0.08 to 1.5 weight percent, expressed as $I^-$ ions and based on the total weight of said composition (A), the application of said composition (A) being preceded or followed by the application of composition (B) containing, in a medium suitable for dyeing said fibers, hydrogen peroxide at a pH ranging from 2 to 12.

8. The process of claim 1 wherein said source of iodide ions is selected from the group consisting of an alkali metal iodide, an alkaline earth metal iodide and ammonium iodide.

9. The process of claim 1 wherein said composition (A) containing, in said medium suitable for dyeing said fibers, said indole derivative, said oxidation dye and a source of iodide ions selected from the group consisting of an alkali metal iodide, an alkaline earth metal iodide and ammonium iodide is applied to said fibers in a first stage and said composition (B) containing hydrogen peroxide in a medium suitable for dyeing said fibers is applied to said fibers in a second stage.

10. The process of claim 1 wherein the hydrogen peroxide content is between 1 and 40 volumes.

11. The process of claim 1 wherein the hydrogen peroxide content is between 2 and 20 volumes.

12. The process of claim 1 wherein the different compositions (A) and (B) are permitted to remain in contact with said fibers for a period of time ranging from 10 seconds to 45 minutes.

13. The process of claim 1 wherein the different compositions (A) and (B) are permitted to remain in contact with said fibers for a period of time ranging from 2 to 25 minutes.

14. The process of claim 1 wherein one or more of said compositions also include at least one adjuvant selected from the group consisting of a fatty amide present in an amount ranging from 0.05 to 10 percent by weight; an anionic, cationic, nonionic or amphoteric surfactant, or a mixture thereof, present in an amount ranging from 0.1 to 50 percent by weight; a thickener present in an amount ranging from 0.1 to 5 percent by weight; a perfume; a sequestering agent; a film-forming agent; a treatment agent; a dispersant; a conditioner; a preservative; an opacifier; and an agent for swelling keratinous fibers.

15. The process of claim 1 wherein said keratinous fibers are human hair.

16. A composition for dyeing keratinous fibers comprising in a medium suitable for dyeing keratinous fibers
(a) at least one indole derivative having the formula

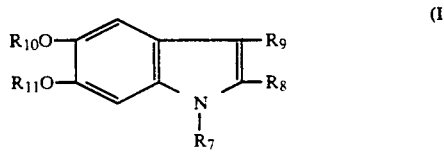

(I)

wherein $R_7$ represents hydrogen, $C_1$–$C_6$ alkyl or $-SiR_{12}R_{13}R_{14}$;

$R_8$ and $R_9$, each independently, represent hydrogen, $C_1$–$C_6$ alkyl, carboxyl, $C_1$–$C_6$ alkoxy carbonyl or $-COOSiR_{12}R_{13}R_{14}$;

$R_{10}$ and $R_{11}$, each independently, represent hydrogen, linear or branched $C_1$–$C_{20}$ alkyl, formyl, linear or branched $C_2$–$C_{20}$ acyl, linear or branched $C_3$–$C_{20}$ alkenoyl, $-SiR_{12}R_{13}R_{14}$, $-P(O)$ $(OR_{15})_2$ or $R_{15}OSO_2$, or $R_{10}$ and $R_{11}$ together with the oxygen atoms to which they are attached form a ring optionally containing a carbonyl group, a methylene group, a thiocarbonyl group, a $>P(O)$ $OR_{15}$ group or a $>CR_{16}R_{17}$ group;

$R_{15}$ and $R_{16}$ represent hydrogen or $C_1$–$C_6$ alkyl;

$R_{17}$ represents $C_1$–$C_6$ alkoxy, monoalkylamino or dialkylamino;

$R_{12}$, $R_{13}$ and $R_{14}$, each independently, represent linear or branched $C_1$–$C_6$ alkyl, and the acid addition salt thereof with an inorganic or organic acid or the corresponding alkali metal, alkaline earth metal or amine salt thereof, said indole derivative being present in an amount ranging from 0.03 to 3 weight percent based on the total weight of said composition, (b) at least one oxidation dye consisting of a rapid oxidation dye which generates a colored compound by oxidation in air within one hour and a coupler, said oxidation dye being present in an amount ranging from 0.25 to 5 weight percent based on the total weight of said composition, and (c) a source of iodide ions present in an amount ranging from 0.08 to 1.5 weight percent, expressed as $I^-$ ions and based on the total weight of said composition.

17. The composition of claim 16 wherein said oxidation dye (b) consists of a coupler.

18. The composition of claim 16 wherein said rapid oxidation dye is a trihydroxylated derivative of benzene, a diaminohydroxybenzene, an aminodihydroxybenzene, an aminohydroxybenzene, a triaminobenzene or a 1,2-dihydroxybenzene.

19. The composition of claim 18 wherein said rapid oxidation dye is 1,2,4-trihydroxybenzene, 1,2,4-trihydroxy-5-($C_1$–$C_6$ alkyl)-benzene, 1,2,3-trihydroxybenzene, 4-aminoresorcinol, 2-amino-1,4-dihydroxybenzene, 2-amino-4-methoxyphenol, 2,4-diaminophenol, 2-aminophenol, 4-methyl-1,2-dihydroxybenzene, 3-methoxycatechol, 1,4-dihydroxy-2-diethylaminobenzene, 2,5-diamino-4-methoxy-1-hydroxybenzene, 4,6-dimethoxy-3-amino-1-hydroxybenzene, 2,6-dimethyl-4-[N-(p-hydroxyphenyl)amino]-1-hydroxybenzene, 1,5-diamino-2-methyl-4-[N-(p-hydroxyphenyl) amino] benzene and a salt thereof.

20. The composition of claim 16 wherein said coupler is a phenol, a meta-diphenol, a meta-aminophenol, an ortho-diphenol, a meta phenylenediamine, a mono- or polyhydroxylated derivative of naphthalene or aminonaphthalene, a pyrazolone or a benzomorpholine.

21. The composition of claim 20 wherein said coupler has the formula

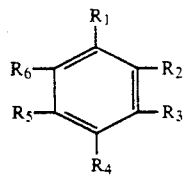
(II)

wherein
  $R_1$ represents OH, amino or amino substituted with at least one $C_1$-$C_6$ hydroxyalkyl,
  $R_3$ and $R_5$, each independently, represent hydrogen, OH, amino, amino substituted with $C_1$-$C_6$ alkyl or $C_1$-$C_6$ hydroxyalkyl,
  $R_2$, $R_4$ and $R_6$ represent hydrogen, $C_1$-$C_6$ alkoxy, $C_1$-$C_6$ alkyl or hydroxyalkoxy, or
  $R_3$ and $R_4$ together form a methylenedioxy group.

22. The composition of claim 21 wherein said coupler is selected from the group consisting of 3-aminophenol, 1,3-dihydroxybenzene, 1,2-dihydroxybenzene, 3-amino-6-methylphenol, 2-methoxy-5-aminophenol, 1,3-diamino-4,6-dimethoxybenzene, 2-methoxy-5[N-(2-hydroxyethyl)amino]phenol, 1,3-diamino-2,6-dimethoxybenzene, 2-methoxy-1-(N-methylamino)-4-(2-hydroxyethyloxy)aminobenzene, 1,3-diamino-4,6-dimethoxybenzene, 1,3-diamino-6-methoxybenzene, 4,6-dimethoxy-1,3-bis[N-(2-hydroxyethyl)amino]benzene, 2,6-dimethoxy-3-[N-(2-hydroxyethyl)amino]-1-aminobenzene, 2,4-dimethoxy-3-[N-(2-hydroxyethyl)amino]-1-aminobenzene, 2-methyl-5-[N-(2-hydroxyethyl)amino]phenol, 4-methoxy-1,3-bis[N-(2-hydroxyethyl)amino]benzene, 3-amino-4-methoxyphenol, 3,4-methylenedioxy-1-aminobenzene, 3,4-methylenedioxy-6-methoxy-1-aminobenzene, 2,6-dimethyl-3-[N-(2-hydroxyethyl)amino]phenol, 2,6-dimethyl-3-aminophenol, 4-ethoxy-1-amino-3-[N,N-bis(2-hydroxyethyl)amino]benzene, (2,4-diaminophenoxy)ethanol, [2-amino-4-(N-methylamino)phenoxy]ethanol, 1-methoxy-2-[N-(2-hydroxyethyl)amino]-4-aminobenzene and their salts.

23. The composition of claim 16 wherein said coupler is 6-aminobenzomorpholine, 6-hydroxybenzomorpholine, 1-naphthol, 1-amino-7-naphthol or a salt thereof.

24. The composition of claim 16 wherein said oxidation dye is selected from the group consisting of 1,2,4-trihydroxybenzene, 1,2,4-trihydroxy-5-methylbenzene, 1,3-dihydroxybenzene, 3-aminophenol, 3-amino-6-methylphenol, 3,4-methylenedioxy-6-methoxy-1-aminobenzene and 1-naphthol.

25. The composition of claim 16 wherein the weight ratio of said indole derivative combined with said oxidation dye relative to said iodide ions ranges from 0.05 to 10.

26. The composition of claim 16 wherein said medium suitable for dyeing said fibers is an aqueous medium comprising water or a mixture of water and an organic solvent, said aqueous medium having a pH ranging from 2 to 7.

27. The composition of claim 16 wherein said medium suitable for dyeing said fibers is an anhydrous solvent.

28. The composition of claim 26 wherein said organic solvent is selected from the group consisting of ethyl alcohol, propyl alcohol, isopropyl alcohol, tert.butyl alcohol, ethylene glycol, ethylene glycol monomethyl ether, ethylene glycol monobutyl ether, ethylene glycol monoethyl ether acetate, propylene glycol, propylene glycol monomethyl ether, dipropylene glycol monomethyl ether and methyl lactate.

29. The composition of claim 27 wherein said anhydrous solvent is selected from the group consisting of ethyl alcohol, propyl alcohol, isopropyl alcohol, tert.butyl alcohol, ethylene glycol, ethylene glycol monomethyl ether, ethylene glycol monobutyl ether, ethylene glycol monoethyl ether acetate, propylene glycol, propylene glycol monomethyl ether, dipropylene glycol monomethyl ether and methyl lactate.

30. A multicompartment kit for use in dyeing keratinous fibers comprising a first compartment housing a composition comprising (i) an indole derivative present in an amount ranging from 0.03 to 3 weight percent based on the total weight of said composition, (ii) an oxidation dye consisting of a rapid oxidation dye which generates a colored compound by oxidation in air within one hour and a coupler, said oxidation dye being present in an amount ranging from 0.25 to 5 weight percent based on the total weight of said composition, and (iii) a source of iodide ions present in an amount ranging from 0.08 to 1.5 weight percent, expressed as $I^-$ ions and based on the total weight of said composition, in a medium suitable for dyeing said keratinous fibers, and a second compartment housing an aqueous hydrogen peroxide composition.

31. The multicompartment kit of claim 30 wherein said aqueous hydrogen peroxide composition has a pH ranging from 2 to 12.

32. The multicompartment kit of claim 30 wherein said aqueous hydrogen peroxide composition has a pH ranging from 2 to 7.

33. A multicompartment kit for use in dyeing keratinous fibers comprising a first compartment housing a composition comprising, in an anhydrous solvent medium, a source of iodide ions present in an amount ranging from 0.08 to 1.5 weight percent, expressed as $I^-$ ions and based on the total weight of said composition, an indole derivative present in an amount ranging from 0.03 to 3 weight percent based on the total weight of said composition and an oxidation dye consisting of a rapid oxidation dye which generates a colored compound by oxidation in air within one hour and a coupler, said oxidation dye being present in an amount ranging from 0.25 to 5 weight percent based on the total weight of said composition; a second compartment housing an aqueous medium suitable for dyeing said kerationous fibers; and a third compartment housing an aqueous hydrogen peroxide composition of 1 to 40 volumes having a pH ranging from 2 to 12; the contents of said second compartment being intended to be admixed with the contents of said first compartment at the time of use.

34. A multicompartment kit for use in dyeing kerationous fibers comprising a first compartment housing a composition comprising, in a medium suitable for dyeing said keratinous fibers, an indole derivative present in an amount ranging from 0.03 to 3 weight percent based on the total weight of said composition and an oxidation dye consisting of a rapid oxidation dye which generates a colored compound by oxidation in air within one hour and a coupler, said oxidation dye being present in an amount ranging from 0.25 to 5 weight percent based on the total weight of said composition; a second compartment housing a composition comprising, in a medium suitable for dyeing said keratinous fibers, a source of iodide ions present in an amount ranging from 0.08 to 1.5 weight percent, expressed as $I^-$ ions and based on the total weight of said composition; and a third compartment housing hydrogen peroxide in an aqueous medium; the contents of said third compartment being intended to be admixed with the contents of said first compartment immediately before use.

* * * * *